US012670988B2

(12) United States Patent
Mason

(10) Patent No.: US 12,670,988 B2
(45) Date of Patent: Jun. 30, 2026

(54) MEDICAL EVENT CONTEXTUALIZATION AND ERROR DETECTION SYSTEM

(71) Applicant: MedExpert International, Inc., Redwood City, CA (US)

(72) Inventor: Maryann H. Mason, Redwood City, CA (US)

(73) Assignee: MedExpert International, Inc., Redwood City, CA (US)

( * ) Notice: Subject to any disclaimer, the term of this patent is extended or adjusted under 35 U.S.C. 154(b) by 0 days.

(21) Appl. No.: 18/807,727

(22) Filed: Aug. 16, 2024

(65) Prior Publication Data
US 2024/0412857 A1    Dec. 12, 2024

Related U.S. Application Data

(63) Continuation of application No. 17/069,722, filed on Oct. 13, 2020, now abandoned.
(Continued)

(51) Int. Cl.
G16H 40/20 (2018.01)
G06F 3/0482 (2013.01)
(Continued)

(52) U.S. Cl.
CPC ........... G16H 40/20 (2018.01); G06F 3/0482 (2013.01); G06F 40/40 (2020.01); G06N 20/00 (2019.01); G06Q 10/10 (2013.01); G06Q 30/0185 (2013.01); G06Q 40/08 (2013.01); G16H 10/20 (2018.01); G16H 15/00 (2018.01); G16H 50/70 (2018.01); G16H 10/60 (2018.01)

(58) Field of Classification Search
CPC ........ G16H 40/20; G16H 10/20; G16H 15/00;
G16H 50/70; G16H 10/60; G06F 3/0482;
G06F 40/40; G06N 20/00; G06Q 10/10;
G06Q 30/0185; G06Q 40/08
USPC ........................................................ 705/2–3
See application file for complete search history.

(56) References Cited

U.S. PATENT DOCUMENTS

| | | | | |
|---|---|---|---|---|
| 2013/0332189 A1* | 12/2013 | Manning | ................ | G16H 10/20 |
| | | | | 705/2 |
| 2019/0341154 A1* | 11/2019 | Kapur | .................... | G06Q 40/08 |
| 2020/0294640 A1* | 9/2020 | Ginsburg | ............... | G16H 40/20 |

OTHER PUBLICATIONS

Sopan et al. "Reducing wrong patient selection errors: exploring the design space of user interface techniques." AMIA . . . Annual Symposium proceedings. AMIA Symposium vol. 2014 1056-65. Nov. 14, 2014 (Year: 2014).*

* cited by examiner

*Primary Examiner* — Joy Chng
(74) *Attorney, Agent, or Firm* — Kolitch Romano Dascenzo Gates LLP

(57) ABSTRACT

A computer-implemented method is described for contextualizing medical events and detecting errors, for example, in claims data. The method may include receiving medical event data from one or more reporting entities, and converting the received data by normalizing and grouping by provider and by medical event. The converted data is presented to the subject of the medical event(s), via a user interface (UI). The UI includes one or more interactive graphical elements (e.g., virtual buttons) each configured to provide feedback on specific aspects of the converted data for the medical event. Based on input from the subject via the UI, it is determined whether the subject believes the received data is correct. If the data is indicated to be incorrect, further investigation may be triggered, and the payor and/or reporting entity may be alerted.

20 Claims, 8 Drawing Sheets

Related U.S. Application Data

(60) Provisional application No. 62/913,453, filed on Oct. 10, 2019.

(51) Int. Cl.
| | | |
|---|---|---|
| *G06F 40/40* | (2020.01) | |
| *G06N 20/00* | (2019.01) | |
| *G06Q 10/10* | (2023.01) | |
| *G06Q 30/018* | (2023.01) | |
| *G06Q 40/08* | (2012.01) | |
| *G16H 10/20* | (2018.01) | |
| *G16H 10/60* | (2018.01) | |
| *G16H 15/00* | (2018.01) | |
| *G16H 50/70* | (2018.01) | |

200

202 — RECEIVE CLAIMS

204 — NORMALIZE, VERIFY, AND GROUP INPUT DATA

206 — PROVIDE ELECTRONIC ACCESS TO CLAIM DATA

208 — ASCERTAIN ACCURACY OF CLAIM DATA

MEDICAL EVENT CONTEXTUALIZATION AND ERROR DETECTION SYSTEM

CROSS-REFERENCES

The following applications and materials are incorporated herein, in their entireties, for all purposes: U.S. patent application Ser. No. 17/069,722, filed Oct. 13, 2020; U.S. Provisional Patent Application Ser. No. 62/913,453, filed Oct. 10, 2019.

FIELD

This disclosure relates to systems and methods for detecting medical billing errors. More specifically, the disclosed embodiments relate to systems and methods for verifying the authenticity of medical events through medical claims and patient feedback.

INTRODUCTION

Explanations of Benefits (EOBs) and reported services utilize required codes which are difficult to understand for some patients. As such, patients may experience issues comprehending their EOB with service information, making medical billing errors even more difficult to detect and/or verify individually by the patient.

SUMMARY

The present disclosure provides systems, apparatuses, and methods relating to detection of medical event errors.

In some embodiments, a computer-implemented method for contextualizing medical events and detecting errors may include: receiving data from one or more reporting entities, wherein the received data includes claim adjudication data relating to one or more medical events at one or more providers; normalizing and grouping the received data by provider and by medical event to produce converted data; generating a user interface (UI) configured to display the converted data, the UI including one or more interactive graphical elements each configured to provide feedback on one or more portions of the converted data; and determining the accuracy of the received data, based on input received via the one or more interactive graphical elements of the UI.

In some embodiments, a data processing system may include: one or more processors; a memory; a software program stored in the memory and configured to aid in detecting errors in medical event data, the software program including a plurality of instructions executable by the one or more processors to: receive the medical event data from one or more reporting entities, wherein the medical event data includes claim adjudication data relating to one or more medical events at one or more providers; normalize and group the medical event data by provider and by medical event to produce converted data; generate a user interface (UI) configured to display the converted data, the UI including one or more interactive graphical elements each configured to provide feedback on one or more portions of the converted data; and determine the accuracy of the medical event data, based on input received via the one or more interactive graphical elements of the UI.

Features, functions, and advantages may be achieved independently in various embodiments of the present disclosure, or may be combined in yet other embodiments, further details of which can be seen with reference to the following description and drawings.

DETAILED DESCRIPTION

Figure 1:
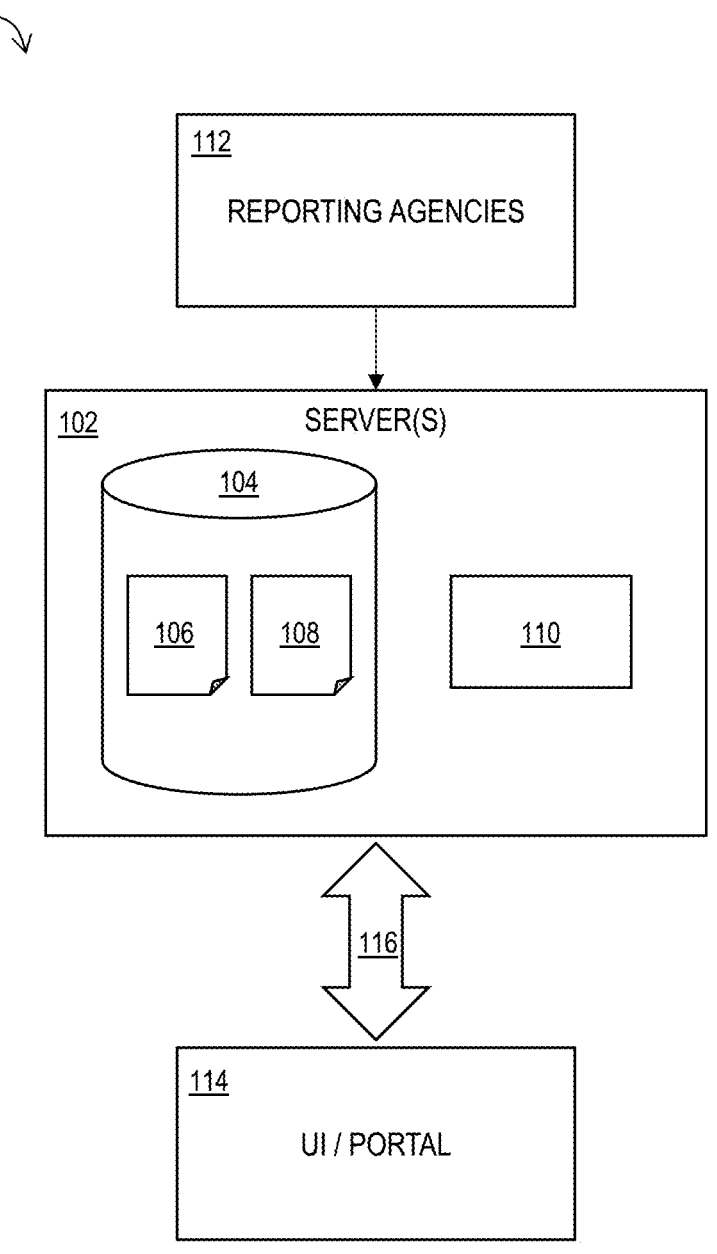
FIG. 1 is a schematic view of an illustrative medical event contextualization and error detection system in accordance with aspects of the present disclosure.

Various aspects and examples of a system for detection of medical event errors (and related methods) are described below and illustrated in the associated drawings. Unless otherwise specified, a medical event contextualization and error detection system in accordance with the present teachings, and/or its various components, may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

This Detailed Description includes the following sections, which follow immediately below: (1) Definitions; (2) Overview; (3) Examples, Components, and Alternatives; (4) Advantages, Features, and Benefits; and (5) Conclusion. The Examples, Components, and Alternatives section is further divided into subsections, each of which is labeled accordingly.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"AKA" means "also known as," and may be used to indicate an alternative or corresponding term for a given element or elements.

"Processing logic" means any suitable device(s) or hardware configured to process data by performing one or more logical and/or arithmetic operations (e.g., executing coded instructions). For example, processing logic may include one or more processors (e.g., central processing units (CPUs) and/or graphics processing units (GPUs)), microprocessors, clusters of processing cores, FPGAs (field-programmable gate arrays), artificial intelligence (AI) accelerators, digital signal processors (DSPs), and/or any other suitable combination of logic hardware.

"Providing," in the context of a method, may include receiving, obtaining, purchasing, manufacturing, generating, processing, preprocessing, and/or the like, such that the object or material provided is in a state and configuration for other steps to be carried out.

"Claims" data includes any instance of medical data, dental data, vision data, pharmaceutical data, and data from any other covered service in the form of medical claims, encounter data, or any data for the reimbursement of services. The contained information includes, but is not limited to, the identification of a patient, a location or renderer of services, and the service or procedure rendered.

"Medical Error" or "Medical Billing Error" includes any incorrect aspect of medical information relating to patient care. The error may be wasteful, fraudulent, neglectful, and/or accidental.

In this disclosure, one or more publications, patents, and/or patent applications may be incorporated by reference. However, such material is only incorporated to the extent that no conflict exists between the incorporated material and the statements and drawings set forth herein. In the event of any such conflict, including any conflict in terminology, the present disclosure is controlling.

Overview

This disclosure relates to systems and methods for the purpose of increasing patient understanding of medical claims, enabling the increased detection of medical billing errors. More specifically, the disclosed embodiments relate to systems and methods for displaying medical event data in a manner patients or subjects can easily understand. This facilitates the authentication of medical events using medical claim data. As used herein, medical claim data may include claims, medical claims, vision claims, insurance claims, encounter data, and/or the like. This may also be referred to collectively as medical event data, or medical event-related data.

In general, a medical event contextualization and error detection system according to the present teachings provides individuals meaningful electronic access to data pertaining to medical insurance claims, health plan encounter data, explanations of benefits (EOBs), and other insurance and health data. Additionally, the medical event error detection system and associated methods may include ascertaining the accuracy and/or validity of the medical data, encounter data, and insurance claims.

Claims may be submitted from a plurality of payors and/or contractually authorized entities. Claims do not have to be paid or adjudicated to be utilized by the system and/or associated methods. The system can operate pre- or post-adjudication and updates the salient information if claims are re-adjudicated.

The claim data is normalized according to a set of expected parameters, such as data characteristic of the subject patient (e.g., health plan, patient identifiers, age, gender, provider, etc.) and/or data characteristic of the specific claim (e.g., insurance codes, health codes, treatment type, etc.). A verification and validation process is established, e.g., with the entity submitting the claim data. The verification and validation process may reconcile claims and/or distinguish between unpaid claims, paid claims, denied claims, adjusted claims, etc. Additionally, or alternatively, the verification and validation process may match and update existing records according to the receipt of new information.

In some examples, an error report is generated if there are any missing or incorrect parameters in the claim data. In some examples, an error report is generated if the claim data has a deviation from the expected size and/or timing of the delivery file. The error report may then be sent to the reporting entity. The report(s) may be submitted to the entity, for example through posting on a secure portal, transmission through secure email, posting the data to an sFTP server, etc.

Data that has been verified and validated is grouped and/or arranged according to similar characteristics (e.g., time, type of service, rendering or institutional provider, etc.). This grouping and/or arranging is configured to increase a patient's ability to understand/contextualize the data and accurately review claims. Many different grouping types exist to provide to maximize the context. The grouping formation is predicted as claims are received and can be changed based on additional claims received. The grouping type (e.g. rehabilitation visits, inpatient stay, DME goods, etc.) has differences and nuances to the UI display to maximize subject responses.

The accuracy of the claim is validated based on information obtained from the subject/user (e.g., the patient). Validation of the claim may occur through one or more of several modalities, including electronic validation and/or telephone validation. In some examples, electronic validation occurs via a secure application on a personal device, such as a computer, tablet, and/or smartphone. Subject validation may also utilize an artificial intelligence (AI)-based tool to pose questions configured to verify the claim's details. Telephone validation may take place over a phone call. This modality may include an automated questioner interacting with the subject, or in some examples, may include a designated representative interacting with the subject to answer questions (e.g., posed by the AI-based tool).

Subject accuracy validation may identify one or more variances in the claim data. These variances may include inaccurate treatments, incorrect costs, incorrect patient/provider, etc. Any gathered information which differs from the claim data may be considered a variance. When a variance is detected, the AI-based tool may automatically provide the user with additional questions. The additional questions may be provided in the same session and/or at another time (e.g., after a time delay).

A digital portal may be accessible to the approved representatives of the entity responsible for claim payment. The portal may display information regarding the claim and/or variances in the claim to the entity. This may be partially obfuscated, altered, or hidden to conform to standards such as HIPAA, HITECH, etc. The system has levels of security to ensure the information provided to subjects is appropriate. These levels are based on standard code sets such as NDC, ICD-10, CPT4, etc. Clients may select to which level they wish to not show information and the decision can change throughout the life of a program. The variance may be captured before or after a claim has been paid.

Depending on the subject's age and legal relationship, a representative for the subject may be able to claim access to the subject's claims data and respond on their behalf. Subjects retain access to all groupings in a repository on the portal. The repository is searchable and includes functions to facilitate conversation between the subject or their representative and a user over the phone, All responses and comments added will remain accessible to the end user. If subjects change health plans, all information will continue to be accessible to the end user for the duration the client is under contract.

A resolution may take place within the administrative portal and/or the entity's appointed division. Reports may be sent to the entity, for example through posting on the secure portal, transmission through secure email, or posting the data to an sFTP server. Authorized representatives may tag various aspects of the data to be tracked when similar data patterns occur on future claims.

Aspects of the medical event error detection system may be embodied as a computer method, computer system, or computer program product. Accordingly, aspects of the medical insurance fraud detection system may take the form of an entirely hardware embodiment, an entirely software embodiment (including firmware, resident software, microcode, and the like), or an embodiment combining software and hardware aspects, all of which may generally be referred to herein as a "circuit," "module," or "system." Furthermore, aspects of the medical insurance fraud detection system may take the form of a computer program product embodied in a computer-readable medium (or media) having computer-readable program code/instructions embodied thereon.

Any combination of computer-readable media may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable non-transitory, tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device.

Program code embodied on a computer-readable medium may be transmitted using any appropriate medium, including but not limited to wireless, wireline, optical fiber cable, RF, and/or the like, and/or any suitable combination of these.

Computer program code for carrying out operations for aspects of the medical insurance fraud detection system may be written in one or any combination of programming languages, including an object-oriented programming language (such as Java, C++), conventional procedural programming languages (such as C), and functional programming languages (such as Haskell). Mobile apps may be developed using any suitable language, including those previously mentioned, as well as Objective-C, Swift, C#, HTML5, and the like. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of the medical insurance fraud detection system may be described below with reference to flowchart illustrations and/or block diagrams of methods, apparatuses, systems, and/or computer program products. Each block and/or combination of blocks in a flowchart and/or block diagram may be implemented by computer program instructions.

The computer program instructions may be programmed into or otherwise provided to processing logic (e.g., a processor of a general purpose computer, special purpose computer, field programmable gate array (FPGA), or other programmable data processing apparatus) to produce a machine, such that the (e.g., machine-readable) instructions, which execute via the processing logic, create means for implementing the functions/acts specified in the flowchart and/or block diagram block(s).

Additionally or alternatively, these computer program instructions may be stored in a computer-readable medium that can direct processing logic and/or any other suitable device to function in a particular manner, such that the instructions stored in the computer-readable medium produce an article of manufacture including instructions which implement the function/act specified in the flowchart and/or block diagram block(s).

The computer program instructions can also be loaded onto processing logic and/or any other suitable device to cause a series of operational steps to be performed on the device to produce a computer-implemented process such that the executed instructions provide processes for implementing the functions/acts specified in the flowchart and/or block diagram block(s).

Any flowchart and/or block diagram in the drawings is intended to illustrate the architecture, functionality, and/or operation of possible implementations of systems, methods, and computer program products according to aspects of the medical insurance fraud detection system. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts.

Examples, Components, and Alternatives

The following sections describe selected aspects of exemplary medical event contextualization and error detection systems as well as related systems and/or methods. The examples in these sections are intended for illustration and should not be interpreted as limiting the scope of the present disclosure. Each section may include one or more distinct embodiments or examples, and/or contextual or related information, function, and/or structure.

A. Illustrative System for Contextualizing Medical Events and Identifying Billing Errors As shown in FIG. 1, this section describes an illustrative medical error detection system 100, which is an example of the medical event contextualization and error detection systems described above.

Medical event contextualization and error detection system 100 includes one or more servers 102 having a memory 104 and one or more processors 110. Memory 104 has stored thereon a secure database 106 having data pertaining to medical insurance claims or encounter data. For example, memory 104 may include a table of claim data (AKA a claim table). The claim table includes the codes and associated descriptions and/or interpretations of the codes as provided by or inferred from insurance companies, medical providers, and/or other third-party sources (AKA reporting agencies 112). Memory 104 may further include instructions 108 for analyzing, verifying, and/or otherwise handling the data stored in database 106. Instructions 108 may be configured to be run on processor(s) 110.

In some examples, database 106 may be stored in a secure (e.g., encrypted) memory in network communication with other components of system 100. For example, instructions 108 may communicate with database 106 solely through the use of a network security protocol and/or application programming interface (API). In this manner, the claim table and other data stored in database 106 may be securely isolated the other components of system 100.

One or more reporting agencies 112 may upload claim data to database 106. Reporting agencies 112 may be healthcare providers (e.g., hospitals, doctor offices, dentists, etc.) and/or insurance providers (e.g., Medicare, Medicaid, Managed Care Organizations, private insurance, etc.). Reporting agencies 112 may provide data pertaining to medical claims such as recipient, services, costs, etc. The claim data may be verified and/or normalized by processor 110 according to instructions 108 before being stored in database 106.

Additionally, server(s) 102 are in network communication with a user through the use of a user interface (UI) 114 (AKA portal). UI 114 is configured to display claim information to the user. UI 114 is additionally configured to provide the user with the means to verify the validity of the claim information, as described below. The network communication (AKA data transfer) between servers 102 and UI 114 may occur through a security filter 116. Security filter 116 may be configured to conform the data to one or more standards such as those set by HIPAA, HITECH, etc. before being made available to the user.

Instructions 108 include the operation of converting (AKA translating) data provided by reporting agencies 112 into a descriptive summary of the medical event (see claim specifics 158 described below). For example, many insurance agencies provide an Explanation of Benefits (EOB) replete with codes and data obfuscation. System 100 is configured to load the claims, insurance, and encounter data to derive the EOB data and other provided data sources and utilize the claim table to produce a descriptive summary (AKA a human-readable format).

Figure 2:
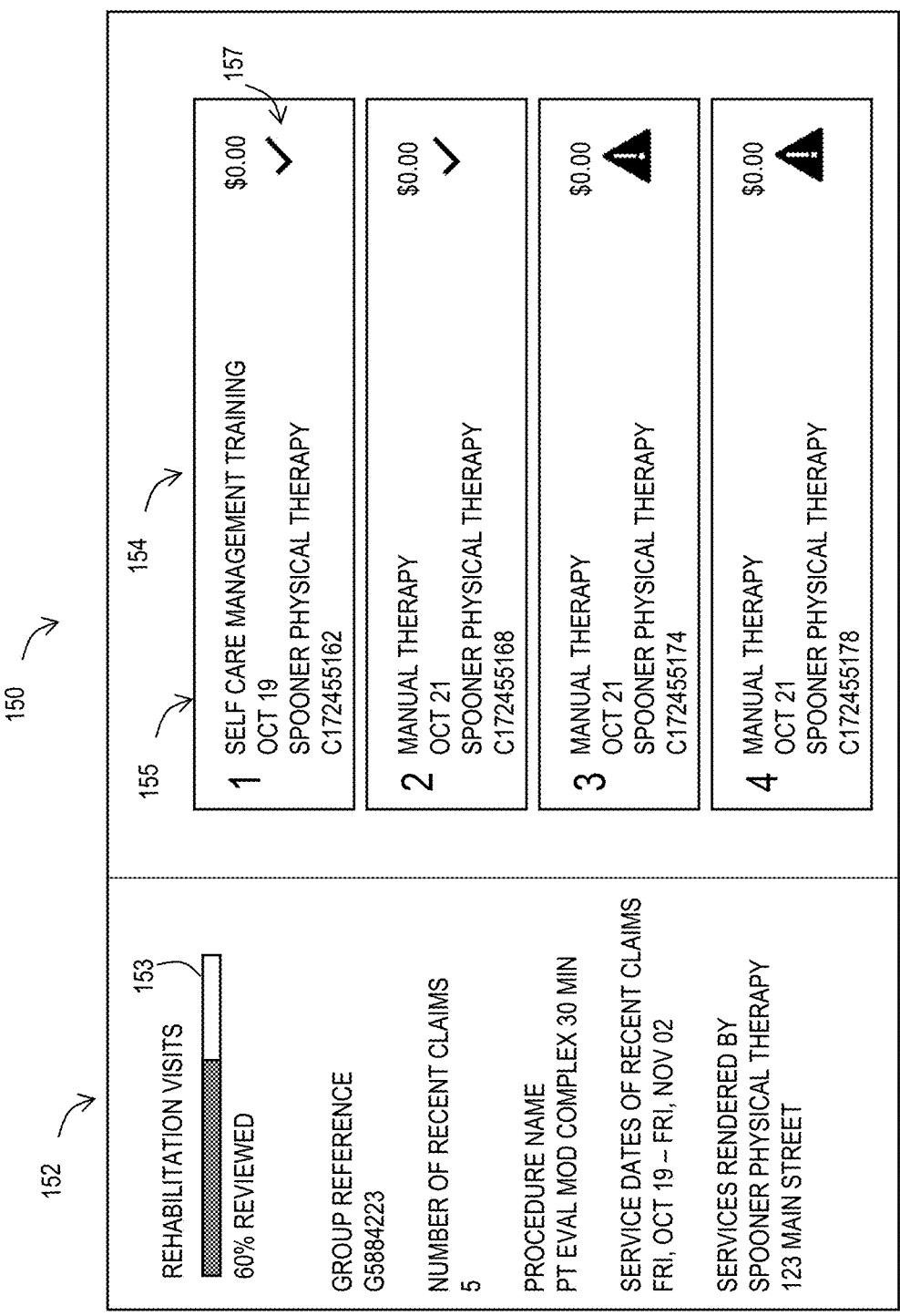
FIG. 2 depicts a portion of an illustrative user interface suitable for use with aspects of the present disclosure.

The user may utilize UI 114 (e.g., through the use of a personal electronic device) to view their claim data, as well as assess the accuracy of the claims. As shown in FIG. 2, UI 114 may include a card 150 including a group label 152 and claim elements 154. The claims may be grouped together as described in the Overview above (and further described below), and information relating to the claims may be displayed on card 150 as claim elements 154. Group label 152 provides the description of the group and allows the user to contextualize the set of claim elements 154 associated with the group. Group label 152 may include a progress bar 153, depicting how far along the user is in the claim reviewing process. As new claims and/or encounters are incurred and added to the group, the label will update accordingly.

Claim groupings 150 may be ordered (e.g. by date of service, priority of claim review, status of claims investigation, etc.) The groupings will be displayed based on a combination of the percentage of claims reviewed, date of payment, date of service start or service end date, etc. If the claim group is not displayed, the claims is still accessible from an available link. The goal is to draw a subject's attention to what will be best to review for the system at large.

Figure 3:
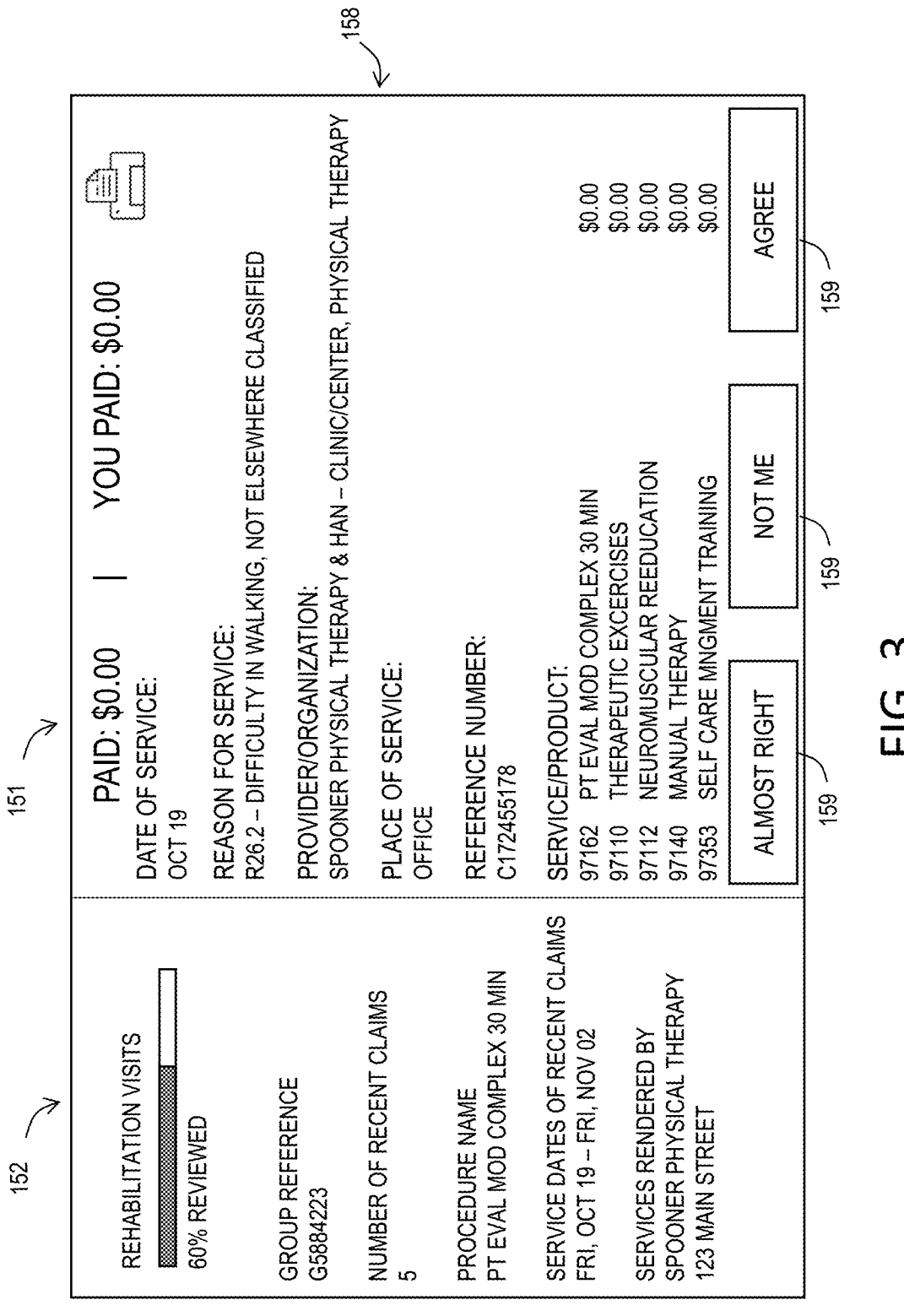
FIG. 3 depicts a portion of an illustrative user interface suitable for use with aspects of the present disclosure.

Claim elements 154 may be ordered (e.g., by date of service, date of payments, payment type, review status, etc.) and/or may be unordered. Each item of claim elements 154 includes a brief overview of claim details 155 and a status indicator 157 indicating whether or not the user has reviewed the specific claim. Certain claims and/or claim information may be left off of card 150 due to privacy constraints (such as reproductive health of minors, psychological health, etc.). Claim elements 154 are presented as a limited preview, with user's initial selection from the claim elements the preview expands accordingly and display additional summary information in the form of a claim summary interface 151 (see FIG. 3).

Claim summary interface 151 includes claim specifics 158 presented as a list of claim- (or encounter)-specific details. Claim specifics 158 are generated from data provided by reporting agencies 112 and comprise the interpretations of the data as specified by the claim table. Claim specifics 158 may replace the Explanation of Benefits provided to the user by existing services. In other words, claim specifics 158 provides an easy-to-read alternative to the raw data provided by the reporting agencies.

Claims summary interface 151 includes interactive claim authentication buttons 159. Claim authentication buttons 159 are configured to enable the user to confirm that the entirety of claim specifics 158 are true (e.g., through the use of a button labeled "agree"). Additionally, claim authentication buttons 159 are configured to enable the user to identify that one or more elements of claim specifics 158 are incorrect (e.g., through the use of a button labeled "almost right"). Additionally, claim authentication buttons 159 are configured to enable the user to identify claim specifics 158 are incorrectly attributed to themselves (e.g., through the use of a button labeled "not me").

In other words, claim summary interface 151 provides the user with an option to selected initial responses with respect to the validity of claim specifics 158. The initial responses include options to agree or select varying levels of variances as described above. These variance selections case the expansion presented in the form of an interactive claim verification interface 156.

Figure 4:
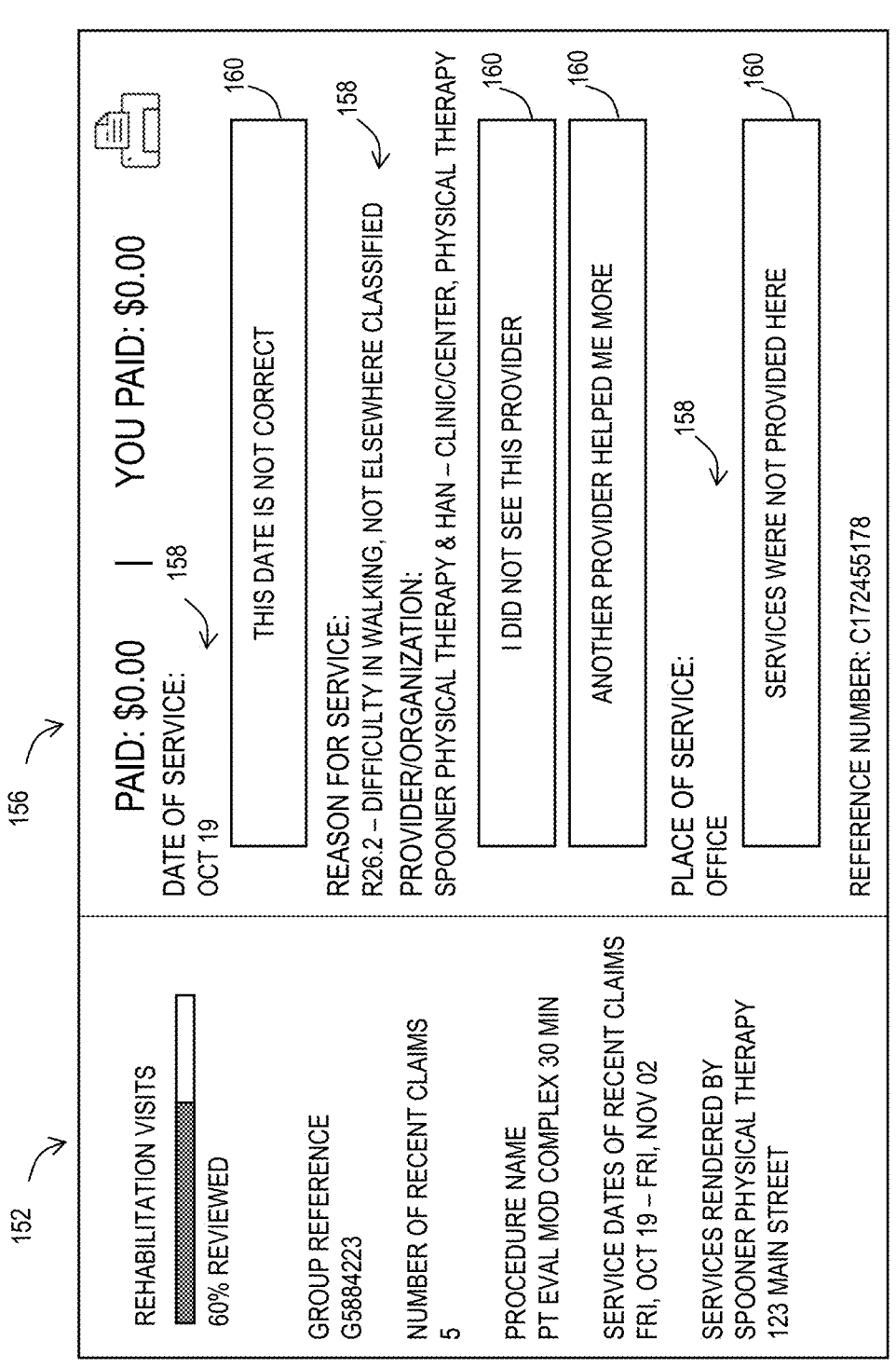
FIG. 4 depicts a portion of an illustrative user interface suitable for use with aspects of the present disclosure.

As shown in FIG. 4, claim verification interface 156 includes claim specifics 158 and interactive verification buttons 160. As described above, system 100 is configured to aggregate all the data provided by reporting agencies 112 and generate a user-friendly report in claim specifics 158. For example, the data provided by reporting agencies 112 (e.g., EOBs) is often obfuscated behind difficult-to-understand codes and short-hands utilized by the reporting agencies. Accordingly, system 100 is configured to interpret the provided data in accordance with the claims table in memory 104, such that a human-readable description may be generated.

Associated with one or more claim specifics 158 is verification buttons 160. The text populated in verification buttons 160 is configured to enable the user to easily and rapidly verify the accuracy of claim specifics 158. System 100 is configured to utilize historical data stored in memory 104, as provided from all users, to generate context-specific verification buttons 160. For example, if a particular health provider has been historically flagged by system 100 for providing a procedure differing from the procedure listed on the claim, verification buttons 160 may include a request pertaining to the validity of the procedure description, such as "This procedure is incorrect."

In another example, system 100 may infer other data, such as location data of the health provider(s) to generate verification buttons. For example, if claim elements 154 include two or more health providers providing service on the same day and the two health providers are geographically distanced from one another by a large distance (e.g., 100 miles), system 100 may provide verification buttons 160 requesting verification of the locations, such as "this location is incorrect," or verification of the date, such as "this date is incorrect."

Accordingly, system 100 is configured to adaptively learn when to flag a claim from historical data. For example, as many users interact with UI 114, a certain specific data parameter (e.g., a specific healthcare provider, healthcare service, date/time of service, etc.) may be frequently identified by the users as incorrect. In subsequent occurrences of the specific data parameter, system 100 may present the claim corresponding to the specific data parameter first in the list provided in claim elements 154. In other words, if a certain healthcare provider is repeatedly flagged by the system as providing incorrect claim data, future claims pertaining to that healthcare provider may be placed first in the list of claims for review by the user. In some examples, future claims pertaining to a flagged data parameter may be outlined, enlarged or otherwise highlighted.

In some examples, a third-party entity may contact the user outside of system 100 (e.g., a telephone call, email, mail, mobile notification, etc.), in the case that a flagged claim requires validation and the user has failed to verify the claim by utilizing system 100.

The user may interact with buttons 160 and accordingly provide relevant feedback. In the case that the user indicates one or more elements of claim specifics 158 is incorrect, system 100 may prompt or trigger an investigation. In some examples, the investigation may include contacting the user, for example with a telephone call, email, or mobile notification. In some examples, the investigation may include prompting the user to provide a written statement, select from a list, or otherwise provide information to the system regarding the validity of the claim. For example, if the location of the service rendered is incorrect, the user may select the appropriate button and, in response, UI 114 may provide the user with an input field such that the user may provide a corrected location.

B. Illustrative Method of Contextualizing Medical Events and Identifying Billing Errors This section describes steps of an illustrative method 200 for detecting medical errors; see FIGS. 5 and 6. Aspects of the medical event contextualization and error detection system described above may be utilized in the method steps described below. Where appropriate, reference may be made to components and systems that may be used in carrying out each step. These references are for illustration, and are not intended to limit the possible ways of carrying out any particular step of the method.

Figure 5:
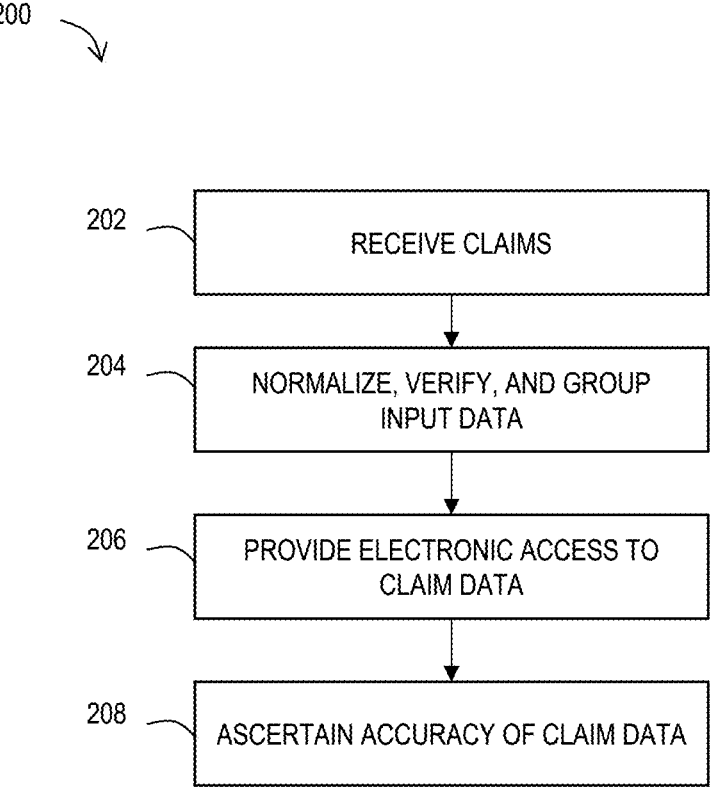
FIG. 5 is a flow chart depicting steps of an illustrative method for providing medical event contextualization and detecting medical errors according to the present teachings.
Figure 6:
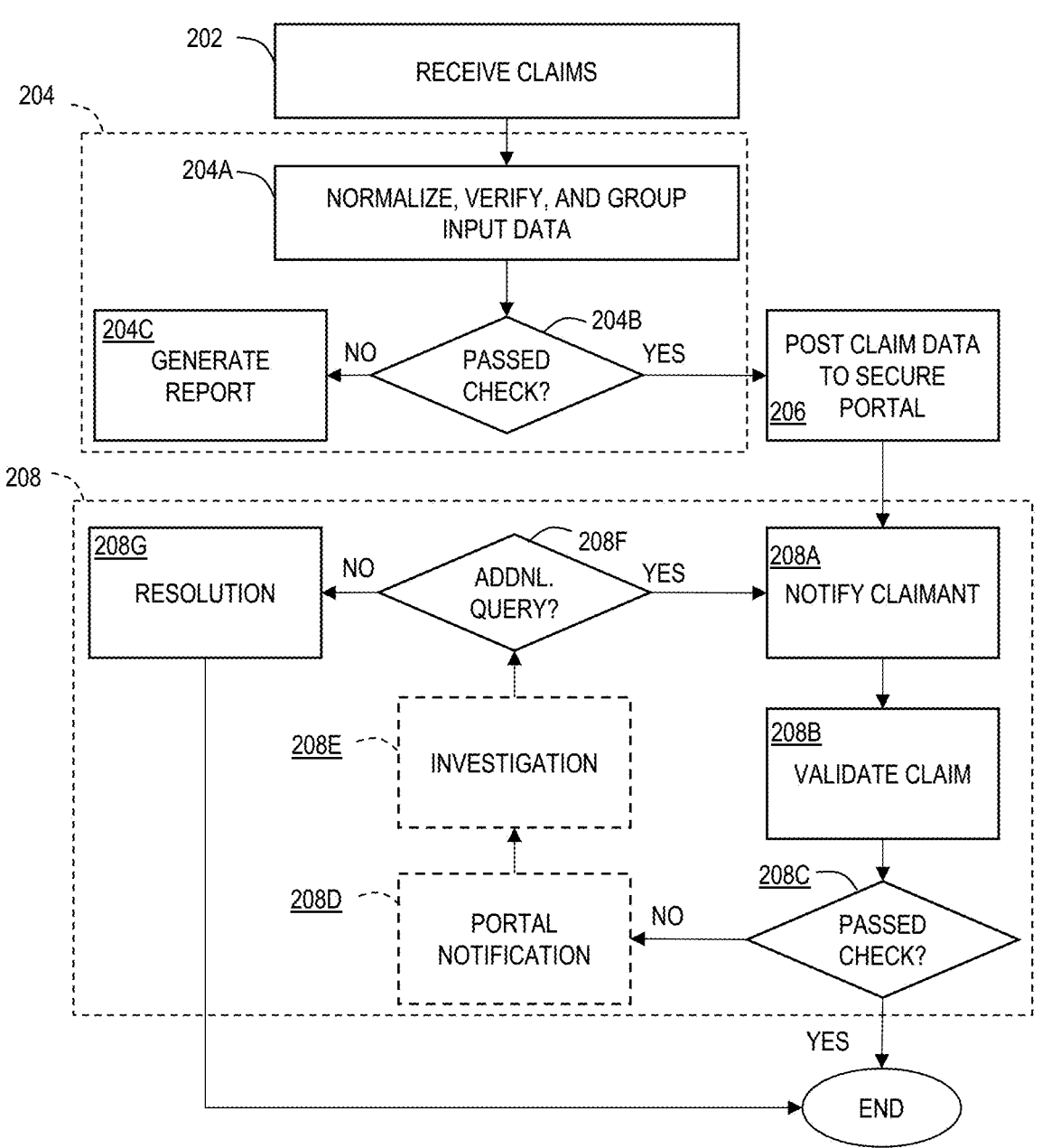
FIG. 6 is a flow chart depicting steps of an illustrative method for providing medical event contextualization and detecting medical errors according to the present teachings.

FIGS. 5 and 6 are flowcharts illustrating steps performed in an illustrative method, and may not recite the complete process or all steps of the method. Although various steps of method 200 are described below and depicted in FIGS. 5 and 6, the steps need not necessarily all be performed, and in some cases may be performed simultaneously or in a different order than the order shown.

Method 200 may be performed with authorization and/or request by a third-party client. For example, the client may comprise a payor or other entity that is responsible for one or more duties (e.g., such as payment or collection) pertaining to a medical bill and/or medical insurance claim.

Step 202 of method 200 includes receiving claim data from a reporting agency. Claim data may be submitted by multiple entities (i.e., a plurality of reporting agencies). The claim data may be supplied electronically (e.g., with a secure reporting portal, email, etc.), and may be stored in memory substantially similar to the memory described above.

Step 204 of method 200 includes normalizing, verifying, and grouping the submitted claim data. Step 204 may include one or more of the following substeps 204A through 204C:

Step 204A includes verifying expected values are present (e.g., patient name, healthcare provider(s), summary of service, etc.). The data may be normalized according to expected parameters such as data characteristic of the patient (e.g., age, race, gender, etc.) and/or data characteristic of the specific claim (e.g., insurance codes, health codes, treatment type, etc.).

Step 204A also includes grouping the data to facilitate ease of comprehension by the patient, e.g., by providing context and details configured to permit a patient/user to accurately evaluate the correctness of the event information. Groups may be created based on one or more of several factors, such as type of service, location of service, rendering provider, diagnosis, etc. Groups can change and can have flexible extensions (e.g. labs associated with inpatient stays can be grouped with the inpatient stay in lieu of other lab work and transportation and lodging can be appended to elements in 152).

Step 204A may also include generating metadata from the claim data and comparing to a table stored on the memory.

Some data may be inferred and/or calculated from the metadata. The data and metadata may be compared to the table to ascertain missing parameters. For example, a health practitioner's name may be inferred from other data sources based on matching identifiers. A location of service can be inferred by other data elements such as metadata on the billing provider. Similarly, this step may identify a threshold deviation in file size and/or delivery time from expected values.

Step 204A may also distinguish between unpaid claims, paid claims, denied claims, and adjusted claims. Furthermore, this step may match and accordingly update records on a database substantially similar to the database described above upon the receipt of new information.

At step 204B, the claims are checked for any issues found in step 204A, if the claim data fails to pass this check (i.e., deviations and/or missing data is identified in step 204A), then the method continues to step 204C. Otherwise, the method continues to step 206. In some examples, steps 204C and 206 may both be performed for the same claim.

At step 204C, a report is generated describing the deviations and/or missing data identified in step 204A. The report may be sent back to the reporting agency and/or sent to the user through the portal.

Step 206 of method 200 includes providing the user with electronic access to claim data. The claim data may be accessed by the user through a UI/portal as described above, for example UI 114. The claim data that has passed the check at 204B may be made available such as through posting to the UI, transmitting through email, posting to a sFTP server, etc. This data may be transformed and/or arranged to conform to security/confidentiality standards (e.g., certain information may be obfuscated if the patient is a child with a sensitive procedure, etc.).

Step 208 of method 200 includes ascertaining the accuracy of the claim data. The claim data made available in step 206C may be verified by the user through the UI. For example, claim data may be presented to the subject/user via the UI, where the UI includes one or more interactive graphical elements (e.g., buttons) each configured to provide feedback on specific aspects of the converted data for a given medical event. Based on input from the subject via the one or more interactive graphical elements of the UI, it can be determined whether the received data is correct (or believed to be correct). Step 208 may comprise some or all of the following sub-steps 208A through 208G:

At step 208A, the user is notified of a new claim data made available. In collaboration with the reporting agency, a notification frequency may be specified for notification of posted claim data on the secure portal. Notifications may occur through a plurality of modalities such as phone, text, fax, email, mail, etc., and may be provided on an ad hoc or scheduled basis.

At step 208B, the accuracy of the claim data is verified by the user. This may include electronic validation and/or telephone validation. Electronic validation may occur via the UI, a secure application on a device, on a computer, on a smartphone, etc. Electronic validation may utilize an artificial intelligence (AI) tool configured to ask verification questions of the user to verify the claim data details. Telephone validation may occur over the phone, for example with a representative qualified to respond to the AI tool. Variance may be considered any gathered information that differs from the claim data. If there is variance in the accuracy of the claim, the AI tool may automatically provide the user with additional questions in the same session and/or with a time delay.

At step 208C, the claim accuracy (as determined in step 208B) is checked. If the claim data is accurate, method 200 ends for the current claim. Method 200 may then be repeated for other claims. If there is variance in the claim data (i.e., if the claim data was found to be inaccurate at step 208B), the method may proceed to optional step 208D.

(Optional) At step 208D, the approved representative of the client may be notified. A portal, substantially similar to the portal described above, detailing the variance may be made accessible to the approved representative of the user. This step may occur before or after the claim has been paid.

(Optional) At step 208E, an investigation may occur in conjunction with the approved representative. The investigation may include a coupling of responses from individuals, trends, and patterns recognized by the AI tool, in concert with input data from the authorized representative. In some examples, step 208D and 208E may be performed together, e.g., as a single step.

At step 208F, the user, approved representative, and/or reporting agency may request to re-query individuals based on responses or identified trends and patterns determined in previous steps. For example, a reporting agency may request a re-query from the user if there was a suspected miss-entry in a previous step. If there is a re-query request, the method may return to step 208A, otherwise the method may continue to step 208G.

At step 208G, the claim variance is resolved. A resolution may include reporting the claim variance to one or more institutions such as a fraud control agency. The resolution may also include reporting the claim variance to the reporting agency. Resolution may take place within an administrative portal. Reporting may occur through several modalities such as posting on UI, transmission through secure email, posting on an sFTP server, etc. Authorized representatives may tag various aspects of the data to be tracked if similar data patterns occur on future claims.

After resolution, method 200 concludes for the claim. A single claim may be processed multiple times using method 200.

C. Illustrative Data Processing System

Figure 7:
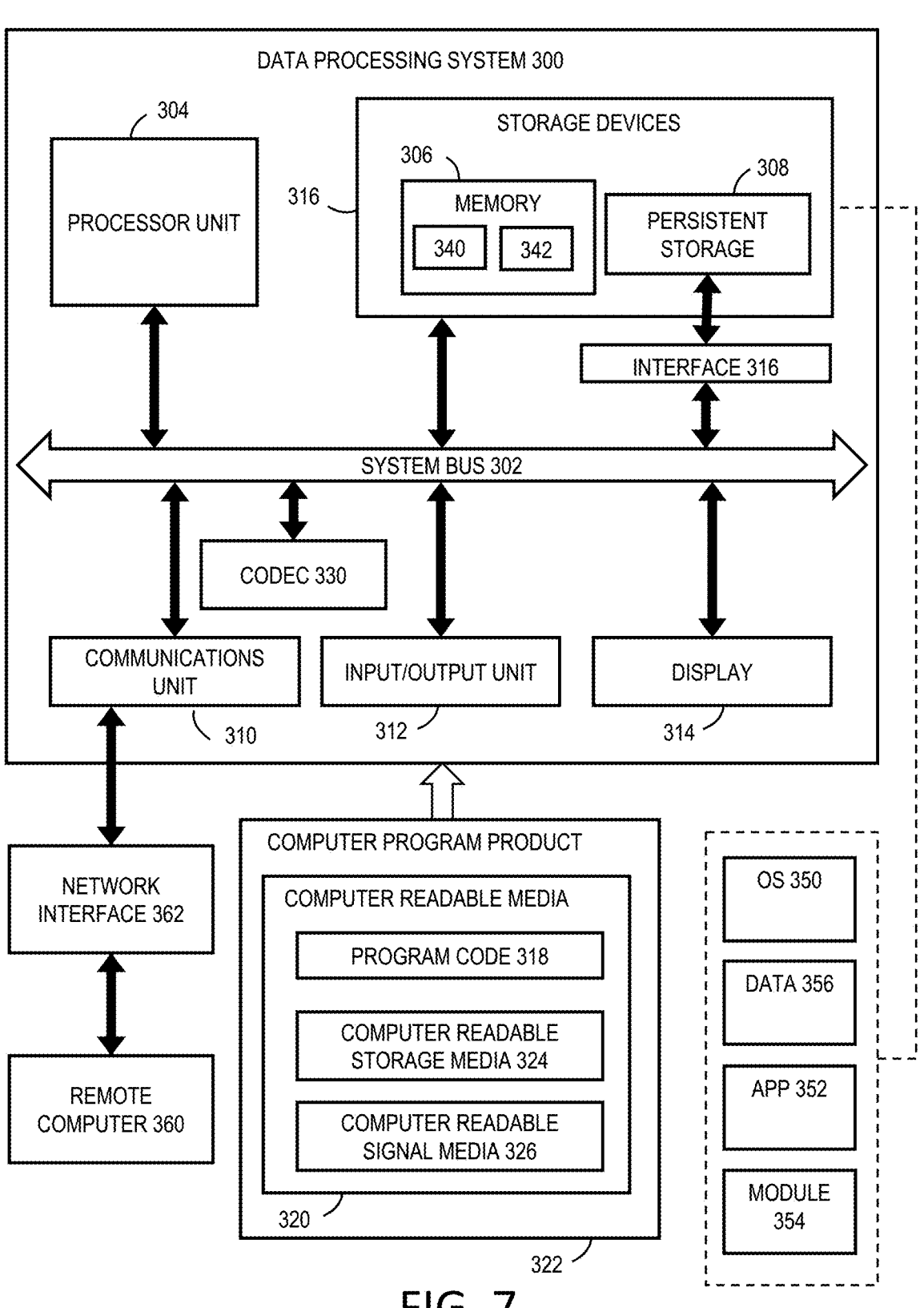
FIG. 7 is a schematic diagram of an illustrative data processing system as described herein.

As shown in FIG. 7, this example describes a data processing system 300 (also referred to as a computer, computing system, and/or computer system) in accordance with aspects of the present disclosure. In this example, data processing system 300 is an illustrative data processing system suitable for implementing aspects of the medical insurance fraud detection system. More specifically, in some examples, devices that are embodiments of data processing systems (e.g., smartphones, tablets, personal computers) may be utilized as any part of the system and/or methods described above.

In this illustrative example, data processing system 300 includes a system bus 302 (also referred to as communications framework). System bus 302 may provide communications between a processor unit 304 (also referred to as a processor or processors), a memory 306, a persistent storage 308, a communications unit 310, an input/output (I/O) unit 312, a codec 330, and/or a display 314. Memory 306, persistent storage 308, communications unit 310, input/output (I/O) unit 312, display 314, and codec 330 are examples of resources that may be accessible by processor unit 304 via system bus 302.

Processor unit 304 serves to run instructions that may be loaded into memory 306. Processor unit 304 may comprise a number of processors, a multi-processor core, and/or a particular type of processor or processors (e.g., a central processing unit (CPU), graphics processing unit (GPU), etc.), depending on the particular implementation. Further, processor unit 304 may be implemented using a number of heterogeneous processor systems in which a main processor is present with secondary processors on a single chip. As another illustrative example, processor unit 304 may be a symmetric multi-processor system containing multiple processors of the same type.

Memory 306 and persistent storage 308 are examples of storage devices 316. A storage device may include any suitable hardware capable of storing information (e.g., digital information), such as data, program code in functional form, and/or other suitable information, either on a temporary basis or a permanent basis.

Storage devices 316 also may be referred to as computer-readable storage devices or computer-readable media. Memory 306 may include a volatile storage memory 340 and a non-volatile memory 342. In some examples, a basic input/output system (BIOS), containing the basic routines to transfer information between elements within the data processing system 300, such as during start-up, may be stored in non-volatile memory 342. Persistent storage 308 may take various forms, depending on the particular implementation.

Persistent storage 308 may contain one or more components or devices. For example, persistent storage 308 may include one or more devices such as a magnetic disk drive (also referred to as a hard disk drive or HDD), solid state disk (SSD), floppy disk drive, tape drive, Jaz drive, Zip drive, flash memory card, memory stick, and/or the like, or any combination of these. One or more of these devices may be removable and/or portable, e.g., a removable hard drive. Persistent storage 308 may include one or more storage media separately or in combination with other storage media, including an optical disk drive such as a compact disk ROM device (CD-ROM), CD recordable drive (CD-R Drive), CD rewritable drive (CD-RW Drive), and/or a digital versatile disk ROM drive (DVD-ROM). To facilitate connection of the persistent storage devices 308 to system bus 302, a removable or non-removable interface is typically used, such as interface 328.

Input/output (I/O) unit 312 allows for input and output of data with other devices that may be connected to data processing system 300 (i.e., input devices and output devices). For example, input device 332 may include one or more pointing and/or information-input devices such as a keyboard, a mouse, a trackball, stylus, touch pad or touch screen, microphone, joystick, game pad, satellite dish, scanner, TV tuner card, digital camera, digital video camera, web camera, and/or the like. These and other input devices may connect to processor unit 304 through system bus 302 via interface port(s) 336. Interface port(s) 336 may include, for example, a serial port, a parallel port, a game port, and/or a universal serial bus (USB).

Output devices 334 may use some of the same types of ports, and in some cases the same actual ports, as input device(s) 332. For example, a USB port may be used to provide input to data processing system 300 and to output information from data processing system 300 to an output device 334. Output adapter 338 is provided to illustrate that there are some output devices 334 (e.g., monitors, speakers, and printers, among others) which require special adapters. Output adapters 338 may include, e.g. video and sounds cards that provide a means of connection between the output device 334 and system bus 302. Other devices and/or systems of devices may provide both input and output capabilities, such as remote computer(s) 360. Display 314 may include any suitable human-machine interface or other mechanism configured to display information to a user, e.g., a CRT, LED, or LCD monitor or screen, etc.

Communications unit 310 refers to any suitable hardware and/or software employed to provide for communications with other data processing systems or devices. While communication unit 310 is shown inside data processing system 300, it may in some examples be at least partially external to data processing system 300. Communications unit 310 may include internal and external technologies, e.g., modems (including regular telephone grade modems, cable modems, and DSL modems), ISDN adapters, and/or wired and wireless Ethernet cards, hubs, routers, etc. Data processing system 300 may operate in a networked environment, using logical connections to one or more remote computers 360. A remote computer(s) 360 may include a personal computer (PC), a server, a router, a network PC, a workstation, a microprocessor-based appliance, a peer device, a smart phone, a tablet, another network note, and/or the like. Remote computer(s) 360 typically include many of the elements described relative to data processing system 300. Remote computer(s) 360 may be logically connected to data processing system 300 through a network interface 362 which is connected to data processing system 300 via communications unit 310. Network interface 362 encompasses wired and/or wireless communication networks, such as local-area networks (LAN), wide-area networks (WAN), and cellular networks. LAN technologies may include Fiber Distributed Data Interface (FDDI), Copper Distributed Data Interface (CDDI), Ethernet, Token Ring, and/or the like. WAN technologies include point-to-point links, circuit switching networks (e.g., Integrated Services Digital networks (ISDN) and variations thereon), packet switching networks, and Digital Subscriber Lines (DSL).

Codec 330 may include an encoder, a decoder, or both, comprising hardware, software, or a combination of hardware and software. Codec 330 may include any suitable device and/or software configured to encode, compress, and/or encrypt a data stream or signal for transmission and storage, and to decode the data stream or signal by decoding, decompressing, and/or decrypting the data stream or signal (e.g., for playback or editing of a video). Although codec 330 is depicted as a separate component, codec 330 may be contained or implemented in memory, e.g., non-volatile memory 342.

Non-volatile memory 342 may include read only memory (ROM), programmable ROM (PROM), electrically programmable ROM (EPROM), electrically erasable programmable ROM (EEPROM), flash memory, and/or the like, or any combination of these. Volatile memory 340 may include random access memory (RAM), which may act as external cache memory. RAM may comprise static RAM (SRAM), dynamic RAM (DRAM), synchronous DRAM (SDRAM), double data rate SDRAM (DDR SDRAM), enhanced SDRAM (ESDRAM), and/or the like, or any combination of these.

Instructions for the operating system, applications, and/or programs may be located in storage devices 316, which are in communication with processor unit 304 through system bus 302. In these illustrative examples, the instructions are in a functional form in persistent storage 308. These instructions may be loaded into memory 306 for execution by processor unit 304. Processes of one or more embodiments of the present disclosure may be performed by processor unit 304 using computer-implemented instructions, which may be located in a memory, such as memory 306.

These instructions are referred to as program instructions, program code, computer usable program code, or computer-readable program code executed by a processor in processor unit 304. The program code in the different embodiments may be embodied on different physical or computer-readable storage media, such as memory 306 or persistent storage 308. Program code 318 may be located in a functional form on computer-readable media 320 that is selectively removable and may be loaded onto or transferred to data processing system 300 for execution by processor unit 304. Program code 318 and computer-readable media 320 form computer program product 322 in these examples. In one example, computer-readable media 320 may comprise computer-readable storage media 324 or computer-readable signal media 326.

Computer-readable storage media 324 may include, for example, an optical or magnetic disk that is inserted or placed into a drive or other device that is part of persistent storage 308 for transfer onto a storage device, such as a hard drive, that is part of persistent storage 308. Computer-readable storage media 324 also may take the form of a persistent storage, such as a hard drive, a thumb drive, or a flash memory, that is connected to data processing system 300. In some instances, computer-readable storage media 324 may not be removable from data processing system 300.

In these examples, computer-readable storage media 324 is a non-transitory, physical or tangible storage device used to store program code 318 rather than a medium that propagates or transmits program code 318. Computer-readable storage media 324 is also referred to as a computer-readable tangible storage device or a computer-readable physical storage device. In other words, computer-readable storage media 324 is media that can be touched by a person.

Alternatively, program code 318 may be transferred to data processing system 300, e.g., remotely over a network, using computer-readable signal media 326. Computer-readable signal media 326 may be, for example, a propagated data signal containing program code 318. For example, computer-readable signal media 326 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 318 may be downloaded over a network to persistent storage 308 from another device or data processing system through computer-readable signal media 326 for use within data processing system 300. For instance, program code stored in a computer-readable storage medium in a server data processing system may be downloaded over a network from the server to data processing system 300. The computer providing program code 318 may be a server computer, a client computer, or some other device capable of storing and transmitting program code 318.

In some examples, program code 318 may comprise an operating system (OS) 350. Operating system 350, which may be stored on persistent storage 308, controls and allocates resources of data processing system 300. One or more applications 352 take advantage of the operating system's management of resources via program modules 354, and program data 356 stored on storage devices 316. OS 350 may include any suitable software system configured to manage and expose hardware resources of computer 300 for sharing and use by applications 352. In some examples, OS 350 provides application programming interfaces (APIs) that facilitate connection of different type of hardware and/or provide applications 352 access to hardware and OS services. In some examples, certain applications 352 may provide further services for use by other applications 352, e.g., as is the case with so-called "middleware." Aspects of present disclosure may be implemented with respect to various operating systems or combinations of operating systems.

The different components illustrated for data processing system 300 are not meant to provide architectural limitations to the manner in which different embodiments may be implemented. One or more embodiments of the present disclosure may be implemented in a data processing system that includes fewer components or includes components in addition to and/or in place of those illustrated for computer 300. Other components shown in FIG. 7 can be varied from the examples depicted. Different embodiments may be implemented using any hardware device or system capable of running program code. As one example, data processing system 300 may include organic components integrated with inorganic components and/or may be comprised entirely of organic components (excluding a human being). For example, a storage device may be comprised of an organic semiconductor.

In some examples, processor unit 304 may take the form of a hardware unit having hardware circuits that are specifically manufactured or configured for a particular use, or to produce a particular outcome or progress. This type of hardware may perform operations without needing program code 318 to be loaded into a memory from a storage device to be configured to perform the operations. For example, processor unit 304 may be a circuit system, an application specific integrated circuit (ASIC), a programmable logic device, or some other suitable type of hardware configured (e.g., preconfigured or reconfigured) to perform a number of operations. With a programmable logic device, for example, the device is configured to perform the number of operations and may be reconfigured at a later time. Examples of programmable logic devices include, a programmable logic array, a field programmable logic array, a field programmable gate array (FPGA), and other suitable hardware devices. With this type of implementation, executable instructions (e.g., program code 318) may be implemented as hardware, e.g., by specifying an FPGA configuration using a hardware description language (HDL) and then using a resulting binary file to (re) configure the FPGA.

In another example, data processing system 300 may be implemented as an FPGA-based (or in some cases ASIC-based), dedicated-purpose set of state machines (e.g., Finite State Machines (FSM)), which may allow critical tasks to be isolated and run on custom hardware. Whereas a processor such as a CPU can be described as a shared-use, general purpose state machine that executes instructions provided to it, FPGA-based state machine(s) are constructed for a special purpose, and may execute hardware-coded logic without sharing resources. Such systems are often utilized for safety-related and mission-critical tasks.

In still another illustrative example, processor unit 304 may be implemented using a combination of processors found in computers and hardware units. Processor unit 304 may have a number of hardware units and a number of processors that are configured to run program code 318. With this depicted example, some of the processes may be implemented in the number of hardware units, while other processes may be implemented in the number of processors.

In another example, system bus 302 may comprise one or more buses, such as a system bus or an input/output bus. Of course, the bus system may be implemented using any suitable type of architecture that provides for a transfer of data between different components or devices attached to the bus system. System bus 302 may include several types of bus structure(s) including memory bus or memory controller, a peripheral bus or external bus, and/or a local bus using any variety of available bus architectures (e.g., Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI)).

Additionally, communications unit 310 may include a number of devices that transmit data, receive data, or both transmit and receive data. Communications unit 310 may be, for example, a modem or a network adapter, two network adapters, or some combination thereof. Further, a memory may be, for example, memory 306, or a cache, such as that found in an interface and memory controller hub that may be present in system bus 302.

D. Illustrative Distributed Data Processing System

Figure 8:
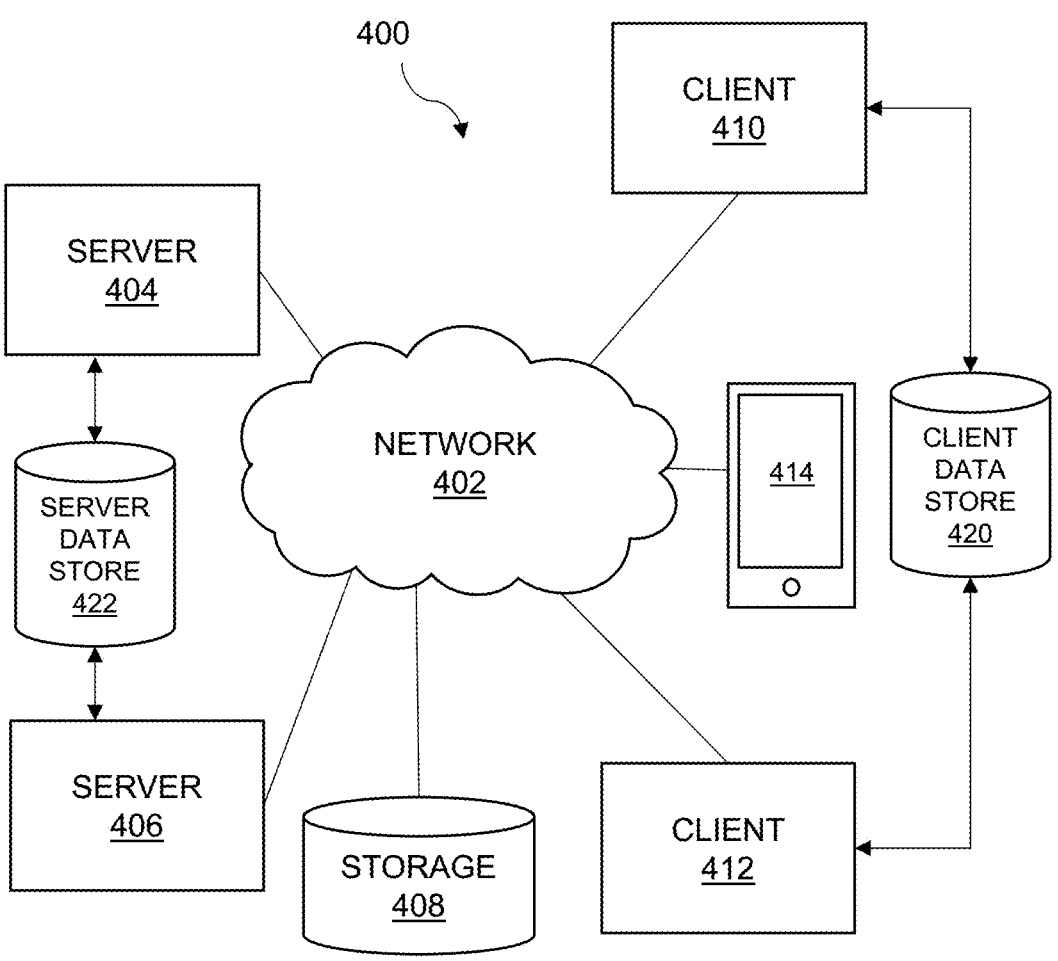
FIG. 8 is a schematic diagram of an illustrative distributed data processing system as described herein.

As shown in FIG. 8, this example describes a general network data processing system 400, interchangeably termed a computer network, a network system, a distributed data processing system, or a distributed network, aspects of which may be included in one or more illustrative embodiments of the medical insurance fraud detection system. For example, communication between the reporting agencies, the server(s), and/or the UI may occur through a network connection and may comprise a distributed data processing system.

It should be appreciated that FIG. 8 is provided as an illustration of one implementation and is not intended to imply any limitation with regard to environments in which different embodiments may be implemented. Many modifications to the depicted environment may be made.

Network system 400 is a network of devices (e.g., computers), each of which may be an example of data processing system 300, and other components. Network data processing system 400 may include network 402, which is a medium configured to provide communications links between various devices and computers connected within network data processing system 400. Network 402 may include connections such as wired or wireless communication links, fiber optic cables, and/or any other suitable medium for transmitting and/or communicating data between network devices, or any combination thereof.

In the depicted example, a first network device 404 and a second network device 406 connect to network 402, as do one or more computer-readable memories or storage devices 408. Network devices 404 and 406 are each examples of data processing system 300, described above. In the depicted example, devices 404 and 406 are shown as server computers, which are in communication with one or more server data store(s) 422 that may be employed to store information local to server computers 404 and 406, among others. However, network devices may include, without limitation, one or more personal computers, mobile computing devices such as personal digital assistants (PDAs), tablets, and smartphones, handheld gaming devices, wearable devices, tablet computers, routers, switches, voice gates, servers, electronic storage devices, imaging devices, media players, and/or other networked-enabled tools that may perform a mechanical or other function. These network devices may be interconnected through wired, wireless, optical, and other appropriate communication links.

In addition, client electronic devices 410 and 412 and/or a client smart device 414, may connect to network 402. Each of these devices is an example of data processing system 300, described above regarding FIG. 7. Client electronic devices 410, 412, and 414 may include, for example, one or more personal computers, network computers, and/or mobile computing devices such as personal digital assistants (PDAs), smart phones, handheld gaming devices, wearable devices, and/or tablet computers, and the like. In the depicted example, server 404 provides information, such as boot files, operating system images, and applications to one or more of client electronic devices 410, 412, and 414. Client electronic devices 410, 412, and 414 may be referred to as "clients" in the context of their relationship to a server such as server computer 404. Client devices may be in communication with one or more client data store(s) 420, which may be employed to store information local to the clients (e.g., cookie(s) and/or associated contextual information). Network data processing system 400 may include more or fewer servers and/or clients (or no servers or clients), as well as other devices not shown.

In some examples, first client electric device 410 may transfer an encoded file to server 404. Server 404 can store the file, decode the file, and/or transmit the file to second client electric device 412. In some examples, first client electric device 410 may transfer an uncompressed file to server 404 and server 404 may compress the file. In some examples, server 404 may encode text, audio, and/or video information, and transmit the information via network 402 to one or more clients.

Client smart device 414 may include any suitable portable electronic device capable of wireless communications and execution of software, such as a smartphone or a tablet. Generally speaking, the term "smartphone" may describe any suitable portable electronic device configured to perform functions of a computer, typically having a touchscreen interface, Internet access, and an operating system capable of running downloaded applications. In addition to making phone calls (e.g., over a cellular network), smartphones may be capable of sending and receiving emails, texts, and multimedia messages, accessing the Internet, and/or functioning as a web browser. Smart devices (e.g., smartphones) may include features of other known electronic devices, such as a media player, personal digital assistant, digital camera, video camera, and/or global positioning system. Smart devices (e.g., smartphones) may be capable of connecting with other smart devices, computers, or electronic devices wirelessly, such as through near field communications (NFC), BLUETOOTH®, WiFi, or mobile broadband networks. Wireless connectively may be established among smart devices, smartphones, computers, and/or other devices to form a mobile network where information can be exchanged.

Data and program code located in system 400 may be stored in or on a computer-readable storage medium, such as network-connected storage device 408 and/or a persistent storage 308 of one of the network computers, as described above, and may be downloaded to a data processing system or other device for use. For example, program code may be stored on a computer-readable storage medium on server computer 404 and downloaded to client 410 over network 402, for use on client 410. In some examples, client data store 420 and server data store 422 reside on one or more storage devices 408 and/or 308.

Network data processing system 400 may be implemented as one or more of different types of networks. For example, system 400 may include an intranet, a local area network (LAN), a wide area network (WAN), or a personal area network (PAN). In some examples, network data processing system 400 includes the Internet, with network 402 representing a worldwide collection of networks and gateways that use the transmission control protocol/Internet protocol (TCP/IP) suite of protocols to communicate with one another. At the heart of the Internet is a backbone of high-speed data communication lines between major nodes or host computers. Thousands of commercial, governmental, educational and other computer systems may be utilized to route data and messages. In some examples, network 402 may be referred to as a "cloud." In those examples, each server 404 may be referred to as a cloud computing node, and client electronic devices may be referred to as cloud consumers, or the like. FIG. 8 is intended as an example, and not as an architectural limitation for any illustrative embodiments.

E. Selected Embodiments and Claim Concepts

This section describes additional aspects and features of a medical event contextualization and error detection system, presented without limitation as a series of paragraphs, some or all of which may be alphanumerically designated for clarity and efficiency. Each of these paragraphs can be combined with one or more other paragraphs, and/or with disclosure from elsewhere in this application, including the attached appendix, in any suitable manner. Some of the paragraphs below may expressly refer to and further limit other paragraphs, providing without limitation examples of some of the suitable combinations.

A0. A computer-implemented method for contextualizing medical events and detecting errors, the method comprising:

receiving data from one or more reporting entities, wherein the received data relates to one or more medical events, each medical event relating to a subject;

converting the received data by normalizing and grouping the received data by provider and by medical event;

presenting to the subject, via a user interface (UI), the converted data relating to at least one of the medical events, the UI including one or more interactive graphical elements each configured to provide feedback on specific aspects of the converted data for the medical event; and determining, based on input from the subject via the one or more interactive graphical elements of the UI, whether the received data is correct.

A1. The method of A0, further comprising:

automatically alerting the reporting entity associated with the received data based on an indication that the received data is not correct.

A2. The method of A0 or A1, wherein the one or more interactive graphical elements each includes a textual label.

A3. The method of A2, wherein the textual label comprises a statement relating to an adjacent aspect of the converted data.

A4. The method of A3, wherein the statement is generated dynamically based on the medical event.

A5. The method of A3, wherein the statement is generated dynamically based on the provider.

A6. The method of any one of paragraphs A0 through A5, wherein converting the received data comprises interpreting the received data using a stored table of plain language translations of known terminology associated with the received data.

A7. The method of any one of paragraphs A0 through A6, wherein the UI is presented to the subject over a computer network.

A8. The method of any one of paragraphs A0 through A7, wherein the one or more interactive graphical elements comprise a virtual button.

A9. The method of any one of paragraphs A0 through A8, wherein the data received from the one or more reporting entities comprises a combination of claim data and encounter data.

A10. The method of any one of paragraphs A0 through A9, further comprising providing a repository for the subject to review all medical event-related information and their previous responses and comments to reviewed medical events data.

B0. A data processing system, comprising:

one or more processors;

a memory;

a software program stored in the memory and configured to aid in detecting errors in medical event data, the software program including a plurality of instructions executable by the one or more processors to:

receive the medical event data from one or more reporting entities, wherein the medical event data relates to one or more medical events, each medical event relating to a subject;

convert the medical event data by normalizing and grouping the medical event data by provider and by medical event;

present, via a user interface (UI), the converted data relating to at least one of the medical events, the UI including one or more interactive graphical elements each configured to provide feedback on specific aspects of the converted data for the medical event; and determine, based on input received via the one or more interactive graphical elements of the UI, whether the medical event data is correct.

B1. The system of B0, wherein the plurality of instructions are further executable to:

automatically alert the reporting entity associated with the medical event data based on an indication that the medical event data is not correct.

B2. The system of B0 or B1, wherein the one or more interactive graphical elements each includes a textual label.

B3. The system of B2, wherein the textual label comprises a statement relating to an adjacent aspect of the medical event data.

B4. The system of B3, wherein the statement is generated dynamically based on the medical event.

B5. The system of B3, wherein the statement is generated dynamically based on the provider.

B6. The system of any one of paragraphs B0 through B5, wherein converting the medical event data comprises interpreting the medical event data using a stored table of plain language translations of known terminology associated with the medical event data.

B7. The system of any one of paragraphs B0 through B6, wherein the UI is presented to the subject over a computer network.

B8. The system of any one of paragraphs B0 through B7, wherein the one or more interactive graphical elements comprise a virtual button.

B9. The system of any one of paragraphs B0 through B8, wherein the medical event data received from the one or more reporting entities comprises a combination of claim data and encounter data.

Advantages, Features, and Benefits

The different embodiments and examples of the system and methods described herein provide several advantages over known solutions for detecting medical insurance fraud. For example, illustrative embodiments and examples described herein allow for simplified and straightforward verification of the accuracy of insurance claims by the patient, who presumably has intimate knowledge of the actual medical procedures and diagnoses which transpired on the date of service in question.

Additionally, and among other benefits, illustrative embodiments and examples described herein allow the patient to uniquely identify variances in their claims. Identifying issues increases the accountability of organizations, which can reduce health care spending for an organization and/or assist in reducing spending annually for capitated arrangements. The data created by patients responding with variances creates a new data stream which can be subsequently utilized.

Additionally, and among other benefits, illustrative embodiments and examples described herein allow the patient easy access to their explanation of benefits and a secure portal to check, verify, and amend the data regarding their claims. The information provided describes all aspects of the visit in prose rather than codes. The portal provides patients longitudinal access to claim information which persists across health plans and plan changes. For example, the list of providers from whom a patient has received care persists and may be retrieved easily. Furthermore, if a patient forgets their diagnosis after a procedure, the information is easily accessible to further improve care even if they change health plans.

Additionally, and among other benefits, utilizing this system improves patient accountability and encourages better utilization of the health care delivery system.

Additionally, and among other benefits, illustrative embodiments and examples described herein allow multiple departments or agencies to share a common portal facilitating the interoperability of data. By using a common portal to track and evaluate errors, agencies can increase their productivity and leverage all available data.

Additionally, and among other benefits, utilizing this system permits for the investigation of a provider's behavior across state lines, under contracts with different health plans, and generally adds transparency to the billing efforts within the health care delivery system.

Additionally, and among other benefits, utilizing this system does not snare providers based on technicalities surfaced during audits. Investigations are focused on providers who have identified billing issues with select patients. In lieu of auditing, the system is efficient and leverages crowd sourcing as a first means of establishing provider behavior patterns.

Additionally, and among other benefits, the portal offers customization at the client and more granular levels to increase the trustworthiness of the site and customize it to a population. Different clients can set different thresholds.

Additionally, and among other benefits, the portal offers a secure manner in which claim information can be reviewed in a HIPAA and HITECH compliant manner by legal guardians and other in legally binding relationships (e.g. those who are wards of the state, possess power of attorney, etc.). Rights can also be authorized and managed within the system.

No known system or device can perform these functions. However, not all embodiments and examples described herein provide the same advantages or the same degree of advantage.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

The invention claimed is:

1. A computer-implemented method for contextualizing medical events and detecting errors, the method comprising:
   receiving data from one or more reporting entities, wherein the received data includes claim adjudication data relating to one or more medical events at one or more providers;
   normalizing and grouping the received data by provider and by medical event to produce converted data;
   generating a user interface (UI) configured to display the converted data, the UI including one or more interactive graphical elements each configured to provide feedback on one or more portions of the converted data; and
   determining the accuracy of the received data, based on input received via the one or more interactive graphical elements of the UI.

2. The method of claim 1, further comprising:
   automatically alerting the reporting entity associated with the received data based on an indication that the received data is inaccurate.

3. The method of claim 1, wherein one or more of the interactive graphical elements includes a textual label, and wherein the textual label comprises a statement relating to a portion of the converted data.

4. The method of claim 3, wherein the statement is generated dynamically based on a medical event of the one or more medical events.

5. The method of claim 3, wherein the statement is generated dynamically based on a provider of the one or more providers.

6. The method of claim 1, wherein converting the received data comprises interpreting the received data using a stored table of plain language translations of known terminology associated with the received data.

7. The method of claim 1, further comprising presenting the UI to a patient over a computer network.

8. The method of claim 1, wherein one or more of the interactive graphical elements comprises a virtual button.

9. The method of claim 1, further comprising:
   identifying missing data from the received data;

inferring the missing data; and dynamically generating the UI displaying the converted data and the inferred missing data.

10. The method of claim 1, further comprising:

identifying a problem provider of the one or more providers included in the received data based on historical user input data relating to the problem provider; and dynamically generating the UI to flag the problem provider.

11. The method of claim 1, further comprising:

identifying contradictory data in the received data; and dynamically generating the UI to flag the contradictory data.

12. The method of claim 11, wherein dynamically generating the UI to flag the contradictory data includes generating a respective interactive graphical element configured to provide feedback on the contradictory data, wherein the respective interactive graphical element includes a textual label dynamically generated based on the contradictory data.

13. A data processing system, comprising:

one or more processors;

a memory;

a software program stored in the memory and configured to aid in detecting errors in medical event data, the software program including a plurality of instructions executable by the one or more processors to:

receive the medical event data from one or more reporting entities, wherein the medical event data includes claim adjudication data relating to one or more medical events at one or more providers;

normalize and group the medical event data by provider and by medical event to produce converted data;

generate a user interface (UI) configured to display the converted data, the UI including one or more interactive graphical elements each configured to provide feedback on one or more portions of the converted data; and determine the accuracy of the medical event data, based on input received via the one or more interactive graphical elements of the UI.

14. The system of claim 13, wherein the plurality of instructions are further executable to:

automatically alert the reporting entity associated with the medical event data based on an indication that the medical event data is inaccurate.

15. The system of claim 13, wherein one or more of the interactive graphical elements includes a textual label, and wherein the textual label comprises a statement relating to a portion of the medical event data.

16. The system of claim 15, wherein the statement is generated dynamically based on a medical event of the one or more medical events.

17. The system of claim 15, wherein the statement is generated dynamically based on a provider of the one or more providers.

18. The system of claim 13, wherein converting the medical event data comprises interpreting the medical event data using a stored table of plain language translations of known terminology associated with the medical event data.

19. The system of claim 13, wherein the UI is presented to a patient over a computer network.

20. The system of claim 13, wherein one or more of the interactive graphical elements comprises a virtual button.

* * * * *